United States Patent
Brewer et al.

(10) Patent No.: US 7,463,923 B2
(45) Date of Patent: **\*Dec. 9, 2008**

(54) METHOD AND APPARATUS FOR DELIVERING A BIPHASIC DEFIBRILLATION PULSE WITH VARIABLE ENERGY

(75) Inventors: James E. Brewer, Lino Lakes, MN (US); Gary B. Stendahl, Crystal, MN (US); Kenneth F. Olson, Edina, MN (US)

(73) Assignee: Cardiac Science Corporation, Bothell, WA (US)

( * ) Notice: Subject to any disclaimer, the term of this patent is extended or adjusted under 35 U.S.C. 154(b) by 490 days.

This patent is subject to a terminal disclaimer.

(21) Appl. No.: 10/760,040

(22) Filed: Jan. 16, 2004

(65) Prior Publication Data

US 2004/0172072 A1 Sep. 2, 2004

Related U.S. Application Data

(63) Continuation of application No. 10/078,735, filed on Feb. 19, 2002, now abandoned, which is a continuation of application No. 09/678,820, filed on Oct. 4, 2000, now Pat. No. 6,411,846, which is a continuation-in-part of application No. 09/383,561, filed on Aug. 26, 1999, now Pat. No. 6,263,239, which is a continuation-in-part of application No. 08/886,736, filed on Jul. 1, 1997, now Pat. No. 5,968,080.

(60) Provisional application No. 60/021,161, filed on Jul. 1, 1996.

(51) Int. Cl.
*A61N 1/39* (2006.01)
(52) U.S. Cl. ......................................................... 607/5
(58) Field of Classification Search .................. 607/5–8
See application file for complete search history.

(56) References Cited

U.S. PATENT DOCUMENTS 3,706,313 A 12/1972 Milani et al.

(Continued)

FOREIGN PATENT DOCUMENTS

EP 25894/62 12/1962

(Continued)

OTHER PUBLICATIONS

*A Minimal Model of the Monophasic Defibrillation Pulse*, by Mark W. Kroll, Pacing and Clinical Electrophysiology, Futura Publishing Co., vol. 16, No. 4, Part I, pp. 693-827, Apr. 1993.

(Continued)

*Primary Examiner*—Scott M Getzow
(74) *Attorney, Agent, or Firm*—Patterson, Thuente, Skaar & Christensen, P.A.

(57) ABSTRACT

An apparatus and method for determining an optimal transchest external defibrillation waveform that provides for variable energy in the first or second phase of a biphasic waveform that, when applied through a plurality of electrodes positioned on a patient's torso, will produce a desired response in the patient's cardiac cell membranes. The method includes the steps of providing a quantitative model of a defibrillator circuit for producing external defibrillation waveforms, the quantitative model of a patient includes a chest component, a heart component, a cell membrane component and a quantitative description of the desired cardiac membrane response function. Finally, a quantitative description of a transchest external defibrillation waveform that will produce the desired cardiac membrane response function is computed. The computation is made as a function of the desired cardiac membrane response function, the patient model and the defibrillator circuit model.

4 Claims, 7 Drawing Sheets

U.S. PATENT DOCUMENTS

| | | | |
|---|---|---|---|
| 3,857,398 | A | 12/1974 | Rubin |
| 3,886,950 | A | 6/1975 | Ukkestad et al. |
| 4,050,004 | A | 9/1977 | Greatbatch |
| 4,504,773 | A | 3/1985 | Suzuki et al. |
| 4,566,457 | A | 1/1986 | Stemple |
| 4,574,810 | A | 3/1986 | Lerman |
| 4,619,265 | A | 10/1986 | Morgan et al. |
| 4,637,397 | A | 1/1987 | Jones et al. |
| 4,745,923 | A | 5/1988 | Winstrom |
| 4,768,512 | A | 9/1988 | Imran |
| 4,821,723 | A | 4/1989 | Baker, Jr. et al. |
| 4,823,796 | A | 4/1989 | Benson |
| 4,850,357 | A | 7/1989 | Bach, Jr. |
| 4,953,551 | A | 9/1990 | Mehra et al. |
| 4,998,531 | A | 3/1991 | Bocchi et al. |
| 5,083,562 | A | 1/1992 | de Coriolis et al. |
| 5,207,219 | A | 5/1993 | Adams et al. |
| 5,306,291 | A | 4/1994 | Kroll et al. |
| 5,352,239 | A | 10/1994 | Pless |
| 5,372,606 | A | 12/1994 | Lang et al. |
| 5,385,575 | A | 1/1995 | Adams |
| 5,391,186 | A | 2/1995 | Kroll et al. |
| 5,395,395 | A | 3/1995 | Hedberg |
| 5,405,361 | A | 4/1995 | Persson |
| 5,411,525 | A | 5/1995 | Swanson et al. |
| 5,411,526 | A | 5/1995 | Kroll et al. |
| 5,431,686 | A | 7/1995 | Kroll et al. |
| 5,534,015 | A | 7/1996 | Kroll et al. |
| 5,593,427 | A | 1/1997 | Gliner et al. |
| 5,601,612 | A | 2/1997 | Gliner et al. |
| 5,607,454 | A | 3/1997 | Cameron et al. |
| 5,725,560 | A | 3/1998 | Brink |
| 5,891,173 | A | 4/1999 | Brewer |
| 5,908,443 | A | 6/1999 | Brewer et al. |
| 5,968,080 | A | 10/1999 | Brewer et al. |
| 5,991,658 | A | 11/1999 | Brewer et al. |
| 6,263,239 | B1 | 7/2001 | Brewer et al. |

FOREIGN PATENT DOCUMENTS

| | | |
|---|---|---|
| EP | 0 281 219 A | 9/1988 |
| EP | 0 445 800 A1 | 9/1991 |
| EP | 0 487 776 A1 | 6/1992 |
| EP | 0 507 504 A1 | 10/1992 |
| WO | WO 94/27674 | 12/1994 |
| WO | WO 95/51215 | 2/1995 |
| WO | WO 95/09673 | 4/1995 |

OTHER PUBLICATIONS

*A Minimal Model of the Single Capacitor Biphasic Defibrillation Waveform*, by Mark W. Kroll, Pacing and Clinical Electrophysiology, Futura Publishing Co., vol. 17, No. 11, Part I, pp. 1707-1836, Nov. 1994.

*Optimizing Defibrillation Through Improved Waveforms*, by Michael Block and Günter Breithardt, Pacing and Clinical Electrophysiology, Futura Publishing Co., vol. 18, No. 3, Part II, pp. 505-631, Mar. 1995.

*Optimal Truncation of Defibrillation Pulses*, by Werner Imich, Pacing and Clinical Electrophysiology, Future Publishing Co., vol. 18, No. 4, pp. 633-758, Apr. 1995.

*A Conceptual Basis for Defibrillation of Waveforms*, by Brian G. Cleland, Pacing and Clinical Electrophysiology, Futura Publishing Co., vol. 19, No. 8, pp. 1141-1272, Aug. 1996.

*Choosing the Optimal Monophasic and Biphasic Waveforms for Ventricular Defibrillation*, by G.P. Walcott, R.G. Walker, A.W. Cates, W. Krassowka, W.M. Smith, R.E. Ideker, Journal of Cardiovascular Electrophysiology, Futura Publishing Co., vol. 6, No. 9, pp. 737-750, Sep. 1995.

*On The Intensity-Time Relations for Stimulation by Electric Currents I*, by H.A. Blair, The Journal of General Physiology, Rockefeller Institute for Medical Research, vol. 15, pp. 708-729, 1932.

*On The Intensity-Time Relations for Stimulation by Electric Currents II*, H A. Blair, The Journal of General Physiology, Rockefeller Institute for Medical Research, vol. 15, pp. 731-755, 1932.

*Ventricular Defibrillation Using Biphasic Waveforms: The Importance of Phasic Duration*, by A.S.L. Tang, S. Yabe, J.M. Wharton, M. Doker, W.M. Smith, R.E. Ideker, Journal of the American College of Cardiology, American College of Cardiology, vol. 13, No. 1, pp. 207-214, Jan. 1989.

*Improved Defibrillation Thresholds With Large Contoured Epicardial Electrodes and Biphasic Waveforms*, by S.A. Feeser, A.S. L. Tang, K.M. Kavanaugh, D.L. Rollins, W.M. Smith, P.D. Wolf, R.E. Ideker, Circulation, American Heart Association, vol. 76, No. 5, pp. 1176-1184, Nov. 1987.

*Strength-Duration and Probability of Success Curves for Defibrillation With Biphasic Waveforms*, S.A. Feeser, A.S.L. Tang, K.M. Kavanaugh, D.L. Rollins, W.M. Smith, P.D. Wolf, R.E. Ideker, Circulation, American Heart Association, vol. 82, No. 6, pp. 2128-2141, Dec. 19990.

*Truncated Biphasic Pulses for Transthoracic Defibrillation*, by G.H. Bardy, B.E. Gliner, P.J. Kudenchuk, J.E. Poole, G.L. Dolack, G.K. Jones, J. Anderson, C. Troutman, G. Johnson, Circulation, American Heart Association, vol. 91, No. 6, pp. 1768-1774, Mar. 1995.

*Transthoracic Defibrillation of Swine With Monophasic and Biphasic Waveforms*, by B.E. Gliner, T.E. Lyster, S.M. Dillion, G.H. Bardy, Circulation, American Heart Association, vol. 92, No. 6, pp. 1634-1643, Sep. 1995.

*Multicenter Comparison of Truncated Biphasic Shocks and Standard Damped Sine Wave Monophasic Shocks for Transthoracic Ventricular Defibrillation*, G.H. Bardy, F.E. Marchlinkski, A.D. Sharma, S.J. Worley, R.M. Luceri, R. Yee, B.D. Halperin, C.L. Fellows, T.S. Ahern, D.A. Chilson, D.L. Packer, D.J. Wilber, T.A. Mattioni, R. Reddy, R.A. Kronmal, R. Lazzara, Circulation, American Heart Association, vol. 94, No. 10, pp. 2507-2514, Nov. 1995.

*Charge Burping Predicts Optimal Ratios of Phase Duration for Biphasic Defibrillation*, by C.D. Swerdlow, W. Fan, J.E. Brewer, NASPE Abstracts, Sec. 361, not dated.

METHOD AND APPARATUS FOR DELIVERING A BIPHASIC DEFIBRILLATION PULSE WITH VARIABLE ENERGY

RELATED APPLICATIONS

This application is a continuation application of application Ser. No. 10/078,735, filed Feb. 19, 2002, now abandoned entitled "METHOD AND APPARATUS FOR DELIVERING A BIPHASIC DEFIBRILLATION PULSE WITH VARIABLE ENERGY," which is a continuation application of non-provisional application Ser. No. 09/678,820, filed Oct. 4, 2000, now U.S. Pat. No. 6,411,846 entitled METHOD AND APPARATUS FOR DELIVERING A BIPHASIC DEFIBRILLATION PULSE WITH VARIABLE ENERGY, which is a continuation-in-part of application Ser. No. 09/383,561, filed Aug. 26, 1999, now U.S. Pat. No. 6,263,239 entitled METHOD AND APPARATUS FOR DETERMINING THE SECOND PHASE OF EXTERNAL DEFIBRILLATOR DEVICES, which is a continuation-in-part application of application Ser. No. 08/886,736 filed Jul. 1, 1997, now issued U.S. Pat. No. 5,968,080, which is based on provisional patent Application No. 60/021,161, filed Jul. 1, 1996 entitled DYNAMIC SECOND PHASE ($\phi_2$) WITH SELF-CORRECTING CHARGE BURPING FOR EXTERNAL DEFIBRILLATOR DEVICES. The contents of each of the above-identified applications are hereby incorporated by reference.

FIELD OF THE INVENTION

This invention relates generally to an electrotherapy method and apparatus for delivering an electrical pulse to a patient's heart. In particular, this invention relates to a method and apparatus for tailoring a second phase of biphasic waveform delivered by an external defibrillator, to random patients, by performing intelligent calculations and analysis to the results of a first phase segment of a biphasic defibrillation waveform and other parameters pertaining thereto based on theory and practice as disclosed herein.

BACKGROUND OF THE INVENTION

Devices for defibrillating a heart have been known for sometime now. Implantable defibrillators are well accepted by the medical community as effective tools to combat fibrillation for an identified segment of the population. A substantial amount of research in fibrillation and the therapy of defibrillation has been done. Much of the most recent research has concentrated on understanding the effects that a defibrillation shock pulse has on fibrillation to terminate such a condition.

A monophasic waveform is defined to be a single phase, capacitive-discharge, time-truncated, waveform with exponential decay. A biphasic waveform is defined to comprise two monophasic waveforms, separated by time and of opposite polarity. The first phase is designated $\phi_1$ and the second phase is designated $\phi_2$. The delivery of $\phi_1$ is completed before the delivery of $\phi_2$ is begun.

After extensive testing, it has been determined that biphasic waveforms are more efficacious than monophasic waveforms. There is a wide debate regarding the reasons for the increased efficacy of biphasic waveforms over that of monophasic waveforms. One hypothesis holds that $\phi_1$ defibrillates the heart and $\phi_2$ performs a stabilizing action that keeps the heart from refibrillating.

Biphasic defibrillation waveforms are now the standard of care in clinical use for defibrillation with implantable cardioverter-defibrillators (ICDs), due to the superior performance demonstrated over that of comparable monophasic waveforms. To better understand these significantly different outcomes, ICD research has developed cardiac cell response models to defibrillation. Waveform design criteria have been derived from these first principles and have been applied to monophasic and biphasic waveforms to optimize their parameters. These principles-based design criteria have produced significant improvements over the current art of waveforms.

In a two-paper set, Blair developed a model for the optimal design of a monophasic waveform when used for electrical stimulation. (1) Blair, H. A., "On the Intensity-time relations for stimulation by electric currents." I. J. Gen. Physiol. 1932; 15: 709-729. (2) Blair, H. A., "On the Intensity-time Relations for stimulation by electric currents." II. J. Gen. Physiol. 1932; 15: 731-755. Blair proposed and demonstrated that the optimal duration of a monophasic waveform is equal to the point in time at which the cell response to the stimulus is maximal. Duplicating Blair's model, Walcott extended Blair's analysis to defibrillation, where they obtained supporting experimental results. Walcott, et al., "Choosing the optimal monophasic and biphasic waveforms for ventricular defibrillation." J. Cardiovasc Electrophysiol. 1995; 6: 737-750.

Independently, Kroll developed a biphasic model for the optimal design of $\phi_2$ for a biphasic defibrillation waveform. Kroll, M. W., "A minimal model of the single capacitor biphasic defibrillation waveform." PACE 1994; 17:1782-1792. Kroll proposed that the $\phi_2$ stabilizing action removed the charge deposited by $\phi_1$ from those cells not stimulated by $\phi_1$. This has come to be known as "charge burping". Kroll supported his hypothesis with retrospective analysis of studies by Dixon, et al., Tang, et al., and Freese, et al. regarding single capacitor, biphasic waveform studies. Dixon, et al., "Improved defibrillation thresholds with large contoured epicardial electrodes and biphasic waveforms." Circulation 1987; 76:1176-1184; Tang, et al. "Ventricular defibrillation using biphasic waveforms: The Importance of Phasic duration." J. Am. Coll. Cardiol. 1989; 13:207-214; and Feeser, S. A., et al. "Strength-duration and probability of success curves for defibrillation with biphasic waveforms." Circulation 1990; 82: 2128-2141. Again, the Walcott group retrospectively evaluated their extension of Blair's model to $\phi_2$ using the Tang and Feeser data sets. Their finding further supported Kroll's hypothesis regarding biphasic defibrillation waveforms. For further discussions on the development of these models, reference may be made to PCT publications WO 95/32020 and WO 95/09673 and to U.S. Pat. No. 5,431,686.

The charge burping hypothesis can be used to develop equations that describe the time course of a cell's membrane potential during a biphasic shock pulse. At the end of $\phi_1$, those cells that were not stimulated by $\phi_1$ have a residual charge due to the action of $\phi_1$ on the cell. The charge burping model hypothesizes that an optimal pulse duration for $\phi_2$ is that duration that removes as much of the $\phi_1$ residual charge from the cell as possible. Ideally, these unstimulated cells are set back to "relative ground." The charge burping model proposed by Kroll is based on the circuit model shown in FIG. 2b, which is adapted from the general model of a defibrillator illustrated in FIG. 2a.

The charge burping model also accounts for removing the residual cell membrane potential at the end of a $\phi_1$ pulse that is independent of a $\phi_2$. That is, $\phi_2$ is delivered by a set of capacitors separate from the set of capacitors used to deliver $\phi_1$. This charge burping model is constructed by adding a second set of capacitors, as illustrated in FIG. 3. In this figure, $C_1$ represents the $\phi_1$ capacitor set, $C_2$ represents the $\phi_2$ capacitor set $R_H$ represents the resistance of the heart, and the pair $C_M$ and $R_M$ represent membrane series capacitance and resistance of a single cell. The node $V_S$ represents the voltage between the electrodes, while $V_M$ denotes the voltage across the cell membrane.

External defibrillators send electrical pulses to the patient's heart through electrodes applied to the patient's torso. External defibrillators are useful in any situation where there may be an unanticipated need to provide electrotherapy to a patient on short notice. The advantage of external defibrillators is that they may be used on a patient as needed, then subsequently moved to be used with another patient.

However, this important advantage has two fundamental limitations. First, external defibrillators do not have direct contact with the patient's heart. External defibrillators have traditionally delivered their electrotherapeutic pulses to the patient's heart from the surface of the patient's chest. This is known as the transthoracic defibrillation problem. Second, external defibrillators must be able to be used on patients having a variety of physiological differences. External defibrillators have traditionally operated according to pulse amplitude and duration parameters that can be effective in all patients. This is known as the patient variability problem.

The prior art described above effectively models implantable defibrillators, however it does not fully address the transthoracic defibrillation problem nor the patient variability problem. In fact, these two limitations to external defibrillators are not fully appreciated by those in the art. For example, prior art disclosures of the use of truncated exponential monophasic or biphasic shock pulses in implantable or external defibrillators have provided little guidance for the design of an external defibrillator that will successfully defibrillate across a large, heterogeneous population of patients. In particular, an implantable defibrillator and an external defibrillator can deliver a shock pulse of similar form, and yet the actual implementation of the waveform delivery system is radically different.

In the past five years, new research in ICD therapy has developed and demonstrated defibrillation models that provide waveform design rules from first principles. These defibrillation models and their associated design rules for the development of defibrillation waveforms and their characteristics were first developed by Kroll and Imich for monophasic waveforms using effective and rheobase current concepts. (1) Kroll, M. W., "A minimal model of the monophasic defibrillation pulse." PACE 1993; 15: 769. (2) Irnich, W., "Optimal truncation of defibrillation pulses." PACE 1995; 18: 673. Subsequently, Kroll, Walcott, Cleland and others developed the passive cardiac cell membrane response model for monophasic and biphasic waveforms, herein called the cell response model. (1) Kroll, M. W., "A minimal model of the single capacitor biphasic defibrillation waveform." PACE 1994; 17: 1782. (2) Walcott, G. P., Walker, R. G., Cates. A. W., Krassowska, W., Smith, W. M, Ideker R E. "Choosing the optimal monophasic and biphasic waveforms for ventricular defibrillation." J Cardiovasc Electrophysiol 1995; 6:737; and Cleland B G. "A conceptual basis for defibrillation waveforms." PACE 1996; 19:1186).

A significant increase in the understanding of waveform design has occurred and substantial improvements have been made by using these newly developed design principles. Block et al. has recently written a comprehensive survey of the new principles-based theories and their impact on optimizing internal defibrillation through improved waveforms. Block M, Breithardt G., "Optimizing defibrillation through improved waveforms." PACE 1995; 18:526.

There have not been significant developments in external defibrillation waveforms beyond the two basic monophasic waveforms: the damped sine or the truncated exponential. To date, their design for transthoracic defibrillation has been based almost entirely on empirically derived data. It seems that the design of monophasic and biphasic waveforms for external defibrillation has not yet been generally influenced by the important developments in ICD research.

Recently there has been reported research on the development and validation of a biphasic truncated exponential waveform in which it was compared clinically to a damped sine waveform. For additional background, reference may be made to U.S. Pat. Nos. 5,593,427, 5,601,612 and 5,607,454. See also: Gliner B. E., Lyster T. E., Dillon S. M., Bardy G. H., "Transthoracic defibrillation of swine with monophasic and biphasic waveforms." Circulation 1995; 92:1634-1643; Bardy G. H., Gliner B. E., Kudenchuk P. J., Poole J. E., Dolack G. L., Jones G. K., Anderson J., Troutman C., Johnson G.; "Truncated biphasic pulses for transthoracic defibrillation." Circulation 1995; 91:1768-1774; and Bardy G. H. et al, "For the Transthoracic Investigators. Multicenter comparison of truncated biphasic shocks and standard damped sine wave monophasic shocks for transthoracic ventricular defibrillation." Circulation 1996; 94:2507-2514. Although the research determined a usable biphasic waveform, there was no new theoretical understanding determined for external waveform design. It appears that external waveform research may develop a "rules-of-thumb by trial and error" design approach much like that established in the early stages of theoretical ICD research. The noted limitations of the transthoracic biphasic waveform may be due in part to a lack of principles-based design rules to determine its waveform characteristics.

There is a continued need for a device designed to perform a quick and automatic adjustment of phase 2 relative to phase 1 if AEDs are to be advantageously applied to random patients according to a cell response model. Further, the model and the device must be adaptable to patient variance and be able to provide automatic adjustment in a dynamic environment.

SUMMARY OF THE INVENTION

The present invention relates to an external defibrillation method and apparatus that addresses the limitations in the prior art. The present invention incorporates three singular practices that distinguish the practice of designing external defibrillators from the practice of designing implantable defibrillators. These practices are 1) designing multiphasic transthoracic shock pulse waveforms from principles based on cardiac electrophysiology, 2) designing multiphasic transthoracic shock pulse waveforms in which each phase of the waveform can be designed without implementation limitations placed on its charging and delivery means by such means for prior waveform phases, and 3) designing multiphasic transthoracic shock pulse waveforms to operate across a wide range of parameters determined by a large, heterogeneous population of patients.

In particular, the present invention provides for a method and apparatus for tailoring and reforming a second phase ($\phi_2$) of a biphasic defibrillation waveform relative to a first phase ($\phi_1$) of the waveform based on intelligent calculations. The method includes the steps of determining and providing a quantitative description of the desired cardiac membrane response function. A quantitative model of a defibrillator circuit for producing external defibrillation waveforms is then provided. Also provided is a quantitative model of a patient which includes a chest component, a heart component and a cell membrane component. A quantitative description of a transchest external defibrillation waveform that will produce the desired cardiac membrane response function is then computed. Intelligent calculations based on the phase 1 cell response is then computed to determine the desired phase 2 waveform. The computation is made as a function of the desired cardiac membrane response function, the patient model and the defibrillator circuit model.

DETAILED DESCRIPTION OF THE PREFERRED EMBODIMENTS

The present invention provides a method and apparatus for tailoring a second phase ($\phi_2$) of a biphasic waveform delivered by an external defibrillator, to random patients, by performing intelligent calculations and analysis to the results of a first phase ($\phi_1$) segment of a biphasic defibrillation waveform and other parameters pertaining thereto. Prior to describing the present invention, a discussion of the development of an external defibrillation model will be given.

External Defibrillator Model

Figure 1A:
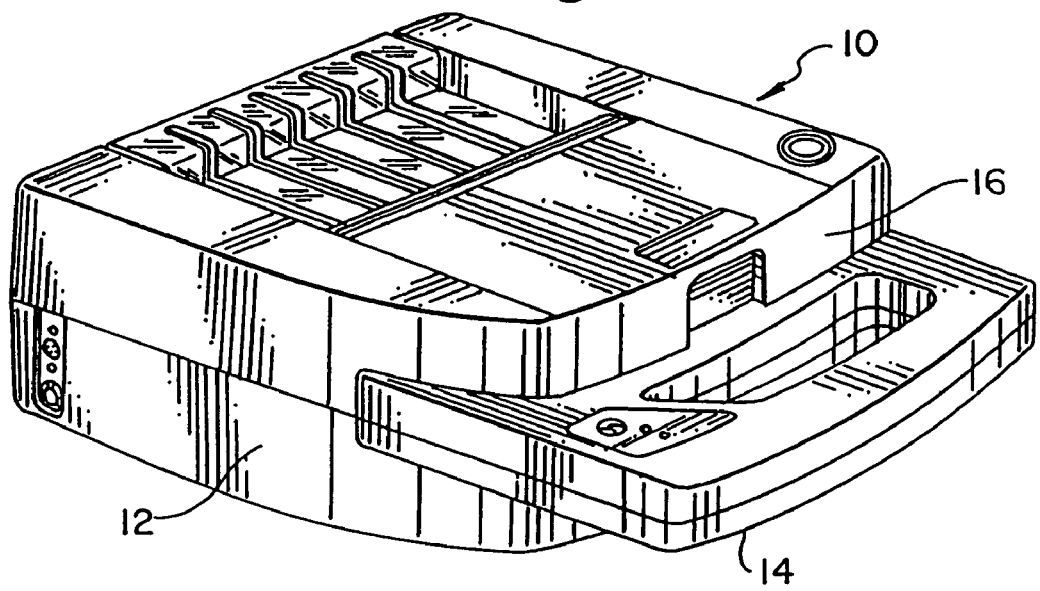
FIGS. 1a and 1b are perspective views of an AED according to the present invention.
Figure 1B:
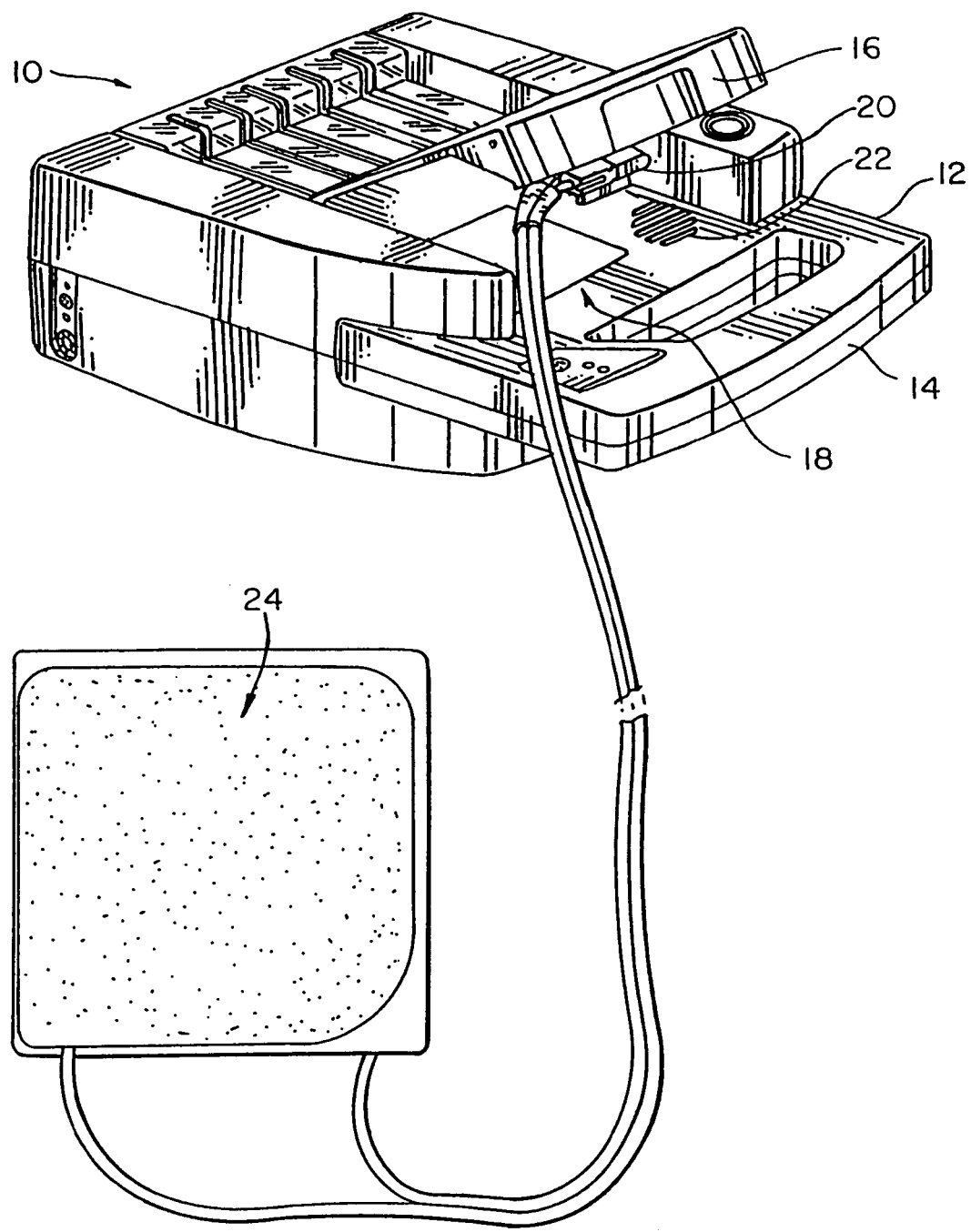
Figure 2A:
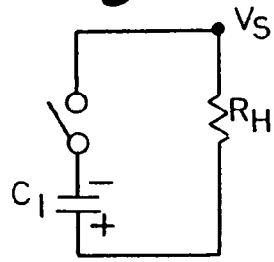
FIG. 2a is a very simplified defibrillator model.
Figure 2B:
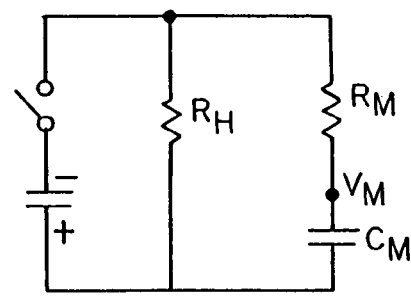
FIG. 2b is a known monophasic defibrillation model.

The apparatus of the present invention is an automated external defibrillator (AED) illustrated in FIGS. 1a and 1b. FIG. 1a illustrates an AED 10, including a plastic case 12 with a carrying handle 14. A lid 16 is provided which covers an electrode compartment 18. An electrode connector 20, a speaker 22 and a diagnostic panel (not shown) are located on case 12 within electrode compartment 18. FIG. 1b illustrates AED 10 having a pair of electrodes 24 connected thereto. Electrodes 24 can be pre-connected to connector 20 and stored in compartment 18.

The operation of AED 10 is described briefly below. A rescue mode of AED 10 is initiated when lid 16 is opened to access electrodes 24. The opening of lid 16 is detected by AED 10 to effectively turn on the device. AED 10 then quickly runs a short test routine. After electrodes 24 have been placed on the patient, AED 10 senses patient specific parameters, such as impedance, voltage, current, charge or other measurable parameters of the patient. The patient specific parameters are then utilized in the design of optimal waveforms as will be described below.

If a shockable condition is detected through electrodes 24, a plurality of capacitors inside of AED 10 are charged from an energy source, typically a detachable battery pack. Based upon the patient specific parameters sensed, the duration and other characteristics of a discharge waveform are then calculated. The energy stored in AED 10 is then discharged to the patient through electrodes 24.

For a more detailed description of the physical structure of AED 10 or the process involved in sensing, charging, shocking and testing, reference should be made to Applicant's issued U.S. Pat. No. 5,645,571, which is assigned to the assignee of the present invention, the disclosure of which is herein incorporated by reference.

In the present invention it is not assumed that both phases of a biphasic waveform are delivered using the same set of capacitors or that both phases of a biphasic waveform are delivered using the capacitor set in the same electrical configuration, although such an embodiment is considered within the spirit and scope of the present invention.

Transthoracic defibrillation is generally performed by placing electrodes on the apex and anterior positions of the chest wall. With this electrode arrangement, nearly all current passing through the heart is conducted by the lungs and the equipotential surfaces pass through the myocardium normal to the electrode axis. The present invention uses the transthoracic charge burping model to develop design equations that describe the time course of a cell's membrane potential during a transthoracic biphasic shock pulse. These equations are then used to create equations that describe the design of monophasic and biphasic shock pulses for transchest defibrillation to optimize the design of $\phi_1$ for defibrillating and the design of $\phi_2$ for stabilizing. These optimizing shock pulse design equations are called design rules.

According to the present invention, the main series pathway for current is to pass through the chest wall, the lungs, and the heart. Additionally, there are two important shunting pathways in parallel with the current pathway through the heart. These shunting pathways must be taken into consideration. The lungs shunt current around the heart through a parallel pathway. The second shunting pathway is provided by the thoracic cage. The resistivity of the thoracic cage and the skeletal muscle structure is low when compared to lungs. The high resistivity of the lungs and the shunting pathways are characterizing elements of external defibrillation that distinguish the art from intracardiac defibrillation and implantable defibrillation technologies.

Figure 4:
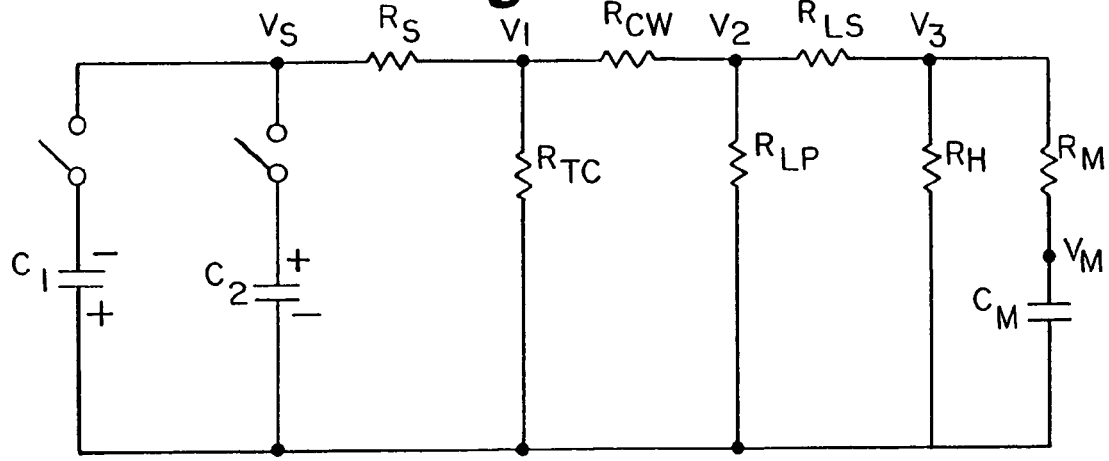
FIG. 4 represents a monophasic or biphasic capacitive-discharge external defibrillation model according to the present invention.

Therefore, in the transthoracic defibrillation model of the present invention illustrated in FIG. 4, there are several resistances in addition to those discussed for the charge burping model above. $R_S$ represents the resistance of the defibrillation system, including the resistance of the defibrillation electrodes. $R_{CW}$ and $R_{LS}$ represent the resistances of the chest wall and the lungs, respectively, in series with resistance of the heart, $R_H$. $R_{TC}$ and $R_{LP}$ represent the resistances of the thoracic cage and the lungs, respectively, in parallel with the resistance of the heart.

The design rules for external defibrillation waveforms are determined in three steps. In the first step, the transchest forcing function is determined. The transchest forcing function is the name that is given to the voltage that is applied across each cardiac cell during an external defibrillation shock. In the second step, the design equations for $\phi_1$ of a shock pulse are determined. The design equations are the equations describing the cell's response to the $\phi_1$ transchest forcing function, the equation describing the optimal $\phi_1$ pulse duration, and the equation describing the optimal $\phi_1$ capacitor. Therefore, step two relates the cell response to the action of a monophasic shock pulse or the first phase of a biphasic shock pulse. This relation is used to determine the optimal design rules and thereby design parameters for the implementation of this phase in an external defibrillator. It will be clear to those in the art that step two is not restricted to capacitor discharge shock pulses and their associated transchest forcing function. Another common implementation of an external defibrillator incorporates a damped sine wave for a shock pulse and can be either a monophasic or biphasic waveform. This type of external defibrillator is modeled by the circuits shown in FIGS. 5a and 5b. In the third step, the design equations for $\phi_2$ of a shock pulse are determined. The design equations are the equations describing the cell's response to the $\phi_2$ transchest forcing function, the equation describing the optimal $\phi_2$ pulse duration and the equation describing the optimal $\phi_2$ capacitor. These design equations are employed to determine the optimal design rules and thereby design parameters of $\phi_2$ of a biphasic shock pulse with respect to how the cell responds to the shock pulse. An important element of this invention is to provide shock pulse waveforms that are designed from a cardiac cell response model developed from first principles and that correctly determines the effects of the chest and its components on the ability of a shock pulse to defibrillate.

The transchest forcing function is determined by solving for the voltage found at node $V_3$ in FIG. 4. The transchest forcing function is derived by solving for $V_3$ using the following three nodal equations:

$$\frac{V_1 - V_S}{R_S} + \frac{V_1}{R_{TC}} + \frac{V_1 - V_2}{R_{CW}} = 0, \quad (1)$$

$$\frac{V_2 - V_1}{R_{CW}} + \frac{V_2}{R_{LP}} + \frac{V_2 - V_3}{R_{LS}} = 0, \text{ and} \quad (2)$$

$$\frac{V_3 - V_2}{R_{LS}} + \frac{V_3}{R_H} + \frac{V_3 - V_M}{R_M} = 0. \quad (3)$$

Equation 1 can be rewritten as $$V_1 \left( \frac{1}{R_S} + \frac{1}{R_{TC}} + \frac{1}{R_{CW}} \right) = \frac{V_S}{R_S} + \frac{V_2}{R_{CW}}. \quad (4A)$$

$$V_1 = \frac{V_S}{R_S \Omega_1} + \frac{V_2}{R_{CW} \Omega_1}, \text{ where } \Omega_1 = \frac{1}{R_S} + \frac{1}{R_{TC}} + \frac{1}{R_{CW}}. \quad (4B)$$

Rewriting equation 2, we have $$V_2 \left( \frac{1}{R_{CW}} + \frac{1}{R_{LP}} + \frac{1}{R_{LS}} \right) = \frac{V_1}{R_{CW}} + \frac{V_3}{R_{LS}} \quad (4C)$$

By substituting equation 4B for $V_1$ into equation 4C, we can solve for $V_2$ as an expression of $V_S$ and $V_3$:

$$V_2 = \frac{V_S}{R_S R_C \Omega_1 \Omega_2 \Omega_{22}} + \frac{V_3}{R_{LS} \Omega_2 \Omega_{22}}, \text{ where} \quad (5)$$

$$\Omega_2 = \frac{1}{R_{LS}} + \frac{1}{R_{LP}} + \frac{1}{R_{CW}}, \text{ and } \Omega_{22} = 1 - \frac{1}{R_{CW}^2 \Omega_1 \Omega_2}.$$

Now solving for $V_3$ as an expression of $V_S$ and $V_M$, equation 3 may be re-arranged as $$V_3 \left( \frac{1}{R_{LS}} + \frac{1}{R_H} + \frac{1}{R_M} \right) = \frac{V_2}{R_{LS}} + \frac{V_M}{R_M} \quad (6)$$

so that $$V_3 = \frac{V_2}{R_{LS} \Omega_3} + \frac{V_M}{R_M \Omega_3} \text{ where } \Omega_3 = \frac{1}{R_{LS}} + \frac{1}{R_H} + \frac{1}{R_M}. \quad (7)$$

Substituting equation 5 for $V_2$ into equation 7, we can solve for $V_3$ as an expression of $V_S$ and $V_M$:

$$V_3 = \frac{V_S}{R_S R_{CW} R_{LS} \Omega_1 \Omega_2 \Omega_{22} \Omega_3 \Omega_{33}} + \frac{V_M}{R_M \Omega_3 \Omega_{33}} \quad (8)$$

where $$\Omega_{33} = 1 - \frac{1}{(R_{LS}^2 \Omega_2 \Omega_{22} \Omega_3)} \quad (9)$$

From equation 8 we define $\Omega_M$ to be:

$$\Omega_M = R_M \Omega_3 \Omega_{33} = R_M \Omega_3 \left( 1 - \frac{1}{(R_{LS}^2 \Omega_2 \Omega_{22} \Omega_3)} \right) \quad (10)$$

$$\Omega_M = R_M \left( \Omega_3 - \frac{1}{R_{LS}^2 \left( \Omega_2 - \frac{1}{R_{CW}^2 \Omega_1} \right)} \right)$$

Figure 5A:
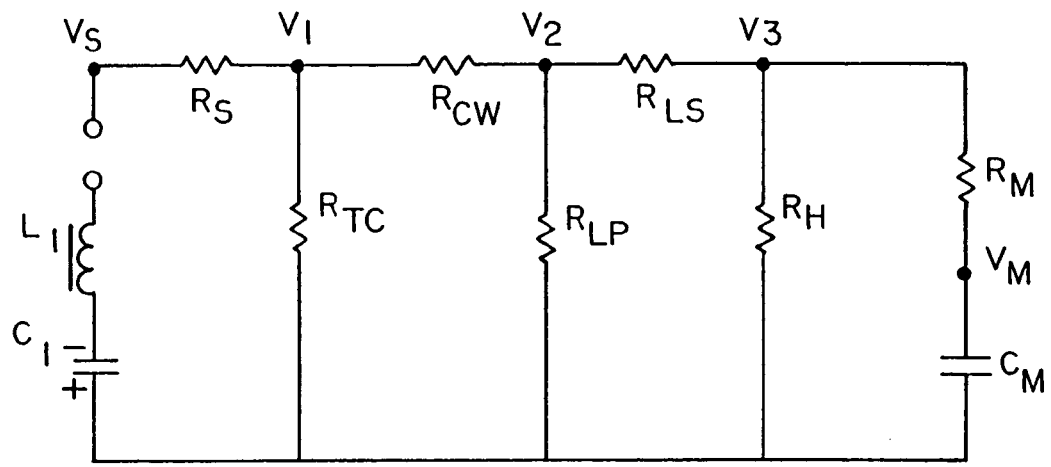
FIG. 5a represents a monophasic capacitor-inductor external defibrillator model according to the present invention.
Figure 5B:
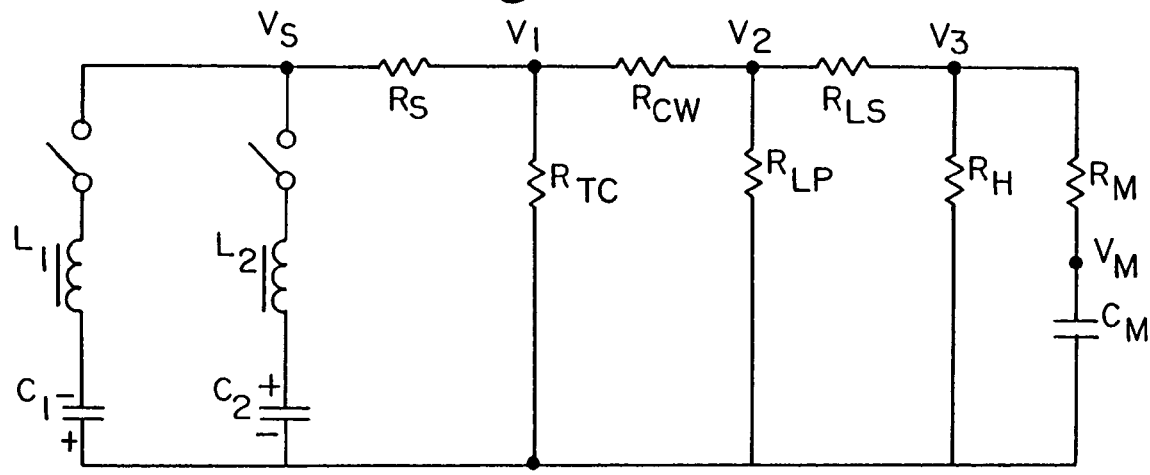
FIG. 5b represents an alternative embodiment of a biphasic capacitor-inductor external defibrillator model according to the present invention.

From equation 8 we also define $\Omega_S$ to be:

$$\Omega_S = R_S R_{CW} R_{LS} \Omega_1 \Omega_2 \Omega_3 \Omega_{22} \Omega_{33} \quad (11)$$

$$\Omega_S = R_S R_{CW} R_{LS} \Omega_1 \Omega_2 \left( 1 - \frac{1}{(R_{CW}^2 \Omega_1 \Omega_2)} \right) \Omega_3 \left( 1 - \frac{1}{(R_{LS}^2 \Omega_2 \Omega_{22} \Omega_3)} \right) \quad (12)$$

$$\Omega_S = R_S R_{CW} R_{LS} \left( \Omega_1 \Omega_2 - \frac{1}{R_{CW}^2} \right) \left( \Omega_3 - \frac{1}{R_{LS}^2 \left( \Omega_2 - \frac{1}{R_{CW}^2 \Omega_1} \right)} \right) \quad (13)$$

so that $V_3 = \frac{V_S}{\Omega_S} + \frac{V_M}{\Omega_M} \quad (14)$ is the general transchest transfer function as shown in FIG. 4 or FIGS. 5a and 5b. Equation 14 encapsulates the transchest elements and their association between the forcing function $V_S$ (which models a defibrillation circuit and the shock pulse) and the cell membrane voltage $V_M$. Therefore, this completes the first step.

The variable $V_S$ may now be replaced with a more specific description of the defibrillation circuitry that implements a shock pulse. For a first example, a monophasic time-truncated, capacitive-discharge circuit may be represented by $V_S = V_1 e^{-t/\tau_1}$, where $V_1$ is the leading-edge voltage for the shock pulse and $\tau_1 = RC_1$, with R determined below.

As shown in FIGS. 5a and 5b, a second example would be a monophasic damped sine wave circuit, represented by $$V_S = V_1 \left( \frac{\tau_{C1}}{\tau_{C1} - \tau_{L1}} \right)(e^{-t/\tau_{C1}} - e^{-t/\tau_{L1}}) \quad (14B)$$

where $V_1$ is the voltage on the charged capacitor $C_1$, $\tau_{C1} = RC_1$ and $\tau_{L1} = L_1/R$. Every step illustrated below may be performed with this and other similar transchest forcing functions which represent defibrillator circuitry.

To proceed with step two, from FIG. 4, nodal analysis provides an equation for $V_M$:

$$C_M \frac{dV_M}{dt} + \frac{V_M - V_3}{R_M} = 0. \quad (15)$$

Rearranging equation 15, we have $$C_M \frac{dV_M}{dt} + \frac{V_M}{R_M} = \frac{V_3}{R_M}. \quad (16)$$

Next, substituting equation 14 as an expression for $V_3$ into equation 16, the cell membrane response is now calculated as follows:

$$C_M \frac{dV_M}{dt} + \frac{V_M}{R_M} = \frac{1}{R_M}\left(\frac{V_S}{\Omega_S} + \frac{V_M}{\Omega_M}\right) \quad (17)$$

$$C_M \frac{dV_M}{dt} + \frac{V_M}{R_M} - \frac{V_M}{R_M \Omega_M} = \quad (18)$$

$$\frac{V_S}{R_M \Omega_S} C_M \frac{dV_M}{dt} + \frac{V_M}{R_M}\left(1 - \frac{1}{\Omega_M}\right) = \frac{V_S}{R_M \Omega_S}$$

Dividing through by $C_M$, and setting $\tau_M = R_M C_M$, then equation 18 becomes $$\frac{dV_M}{dt} + \frac{V_M}{\tau_M}\left(1 - \frac{1}{\Omega_M}\right) = \frac{V_S}{\tau_M}\left(\frac{1}{\Omega_S}\right). \quad (19)$$

Equation 19 is a general ordinary differential equation (ODE) that models the effects of any general forcing function $V_S$ that represents a phase of a shock pulse waveform applied across the chest. The general ODE equation 19 models the effects of a general shock pulse phase $V_S$ on the myocardium, determining cardiac cell response to such a shock pulse phase.

In the equations given below:

$C_1$ equals the capacitance of the first capacitor bank and $V_S = V_1 e^{-t/\tau_1}$;

$C_2$ equals the capacitance of the second capacitor bank and $V_S = V_2 e^{-t/\tau_2}$;

$R = R_S + R_B$, where $R_S$ = System impedance (device and electrodes);

$R_B$ = body impedance (thoracic cage, chest wall, lungs (series, parallel), heart).

To determine body impedance, $R_B$, we see that the series combination of $R_H$ and $R_{LS}$ yields $R_H + R_{LS}$. (FIG. 4). The parallel combination of $R_H + R_{LS}$ and $R_{LP}$ yields:

$$\frac{R_{LP}(R_{LS} + R_H)}{R_{LP} + R_{LS} + R_H}. \quad (20)$$

The series combination of equation 20 and $R_{CW}$ yields:

$$R_{CW} + \frac{R_{LP}(R_{LS} + R_H)}{(R_{LP} + R_{LS} + R_H)}. \quad (21)$$

The parallel combination of equation 21 and $R_{TC}$ yields:

$$R_B = \left[ \frac{R_{TC} R_{CW} + \frac{R_{LP}(R_{LS} + R_H)}{(R_{LP} + R_{LS} + R_H)}}{R_{TC} + R_{CW} + \frac{R_{LP}(R_{LS} + R_H)}{(R_{LP} + R_{LS} + R_H)}} \right] \quad (22)$$

where $R_B$ is the impedance of the body for this model.

The discharge of a single capacitor is modeled by $V_S = V_1 e^{-t/\tau_1}$ for an initial $C_1$ capacitor voltage of $V_1$. Placing $V_S$ into equation 19 gives:

$$\frac{dV_M}{dt} + \frac{V_M}{\tau_M}\left(1 - \frac{1}{\Omega_M}\right) = \frac{V_1 e^{-t/\tau_1}}{\tau_M \Omega_S} \quad (23)$$

where $\tau_M = R_M C_M$ represents the time constant of the myocardial cell in the circuit model, and $\tau_1$, which equals $R_S C_1$, represents the time constant of $\phi_1$. Such a standard linear ODE as equation 23 has the form $$\frac{dy}{dx} + P(X)Y = Q(x).$$

These linear ODEs have an integration factor that equals $e^{\int p dx}$. The general solution to such equations is:

$$Y = e^{-\int p dx}[\int e^{\int p dx} Q dx + c].$$

The ODE in equation 23 models the effects of each phase of a time-truncated, capacitor-discharged shock pulse waveform. Equation 23 is a first-order linear ODE, and may be solved using the method of integration factors, to get:

$$V_{M1}(t) = k e^{-(t/\tau_M)\left(1 - \frac{1}{\Omega_M}\right)} + \left(\frac{V_1}{\Omega_S}\right)\left(\frac{\tau_1}{\tau_1\left(1 - \frac{1}{\Omega_M}\right) - \tau_M}\right) e^{-t/\tau_M}. \quad (24)$$

Equation 24 is an expression of cell membrane potential during $\phi_1$ of a shock pulse. To determine the constant of integration k, the initial value of $V_{M1}$ is assumed to be $V_{M1}(0) = V_G$ ("cell ground"). Applying this initial condition to equation 24, k is found to be $$k = V_G - \left(\frac{V_o}{\Omega_S}\right)\left(\frac{\tau_1}{\tau_1\left(1 - \frac{1}{M}\right) - \tau_M}\right). \quad (25)$$

Assuming $\tau_1 = RC_1$, where $R = R_S + R_B$, then the solution to the initial-value problem for $\phi_1$ is:

$$V_{M1}(t) = V_G e^{-(t/\tau_M)\left(1 - \frac{1}{\Omega_M}\right)} + \left(\frac{V_1}{\Omega_S}\right)\left(\frac{\tau_1}{\tau_1\left(1 - \frac{1}{\Omega_M}\right) - \tau_M}\right)\left(e^{-t/\tau_1} - e^{-(t/\tau_M)\left(1 - \frac{1}{\Omega_M}\right)}\right) \quad (26)$$

Equation 26 describes the residual voltage found on a cell at the end of $\phi_1$.

Assuming $V_G = 0$ and $V_1 = 1$, the solution for cell response to an external shock pulse is $$V_{M1}(t) = \left(\frac{1}{\Omega_S}\right)\left(\frac{\tau_1}{\tau_1\left(1 - \frac{1}{\Omega_M}\right) - \tau_M}\right)\left(e^{-\frac{t}{\tau_1}} - e^{-\left(\frac{t}{\tau_M}\right)\left(1 - \frac{1}{\Omega_M}\right)}\right). \quad (27)$$

We may now determine optimal durations for $\phi_1$ according to criteria for desired cell response. One such design role or criterion is that the $\phi_1$ duration is equal to the time required for the external defibrillator shock pulse to bring the cell response to its maximum possible level. To determine this duration, equation 27 is differentiated and the resulting equation 27B is set to zero. Equation 27B is then solved for the time t, which represents shock pulse duration required to maximize cardiac cell response.

$$\left(\frac{AB}{\tau_M}\right)e^{-Bt/\tau_M} - \left(\frac{A}{\tau_1}\right)e^{-t/\tau_1} = 0, \text{ where} \quad (27B)$$

$$A = \left(\frac{1}{\Omega_S}\right)\left(\frac{\tau_1}{\tau_1\left(1 - \frac{1}{\Omega_M}\right) - \tau_M}\right) \text{ and } B = 1 - \frac{1}{\Omega_M}.$$

Solving for t, the optimal duration $d\phi_1$ for a monophasic shock pulse or $\phi_1$ of a biphasic shock pulse is found to be $$d\phi_1 = \left(\frac{\tau_1 \tau_M}{\tau_1\left(1 - \frac{1}{\Omega_M}\right) - \tau_M}\right)\ln\left(\frac{\tau_1\left(1 - \frac{1}{\Omega_M}\right)}{\tau_M}\right), \quad (27C)$$

where "ln" represents the logarithm to the base e, the natural logarithm.

For $\phi_2$, an analysis almost identical to equations 20 through 27 above is derived. The differences are two-fold. First, a biphasic waveform reverses the flow of current through the myocardium during $\phi_2$. Reversing the flow of current in the circuit model changes the sign on the current. The sign changes on the right hand side of equation 23.

The second difference is the step taken to incorporate an independent $\phi_2$ into the charge burping model. Therefore, the $\phi_2$ ODE incorporates the $C_2$ capacitor set and their associated leading-edge voltage, $V_2$, for the $\phi_2$ portion of the pulse. Then $\tau_2$ represents the $\phi_2$ time constant; $\tau_2 = RC_2$, and $V_S = -V_2 e^{-t/\tau_2}$. Equation 23 now becomes:

$$\frac{dV_M}{dt} + \left(\frac{V_M}{\tau_M}\right)\left(1 - \frac{1}{\Omega_M}\right) = \frac{-V_2 e^{-t/\tau_2}}{\tau_M \Omega_M}. \quad (29)$$

Equation 29 is again a first-order linear ODE. In a similar manner, its general solution is determined to be:

$$V_{M2}(t) = k e^{-(t/\tau_M)\left(1 - \frac{1}{\Omega_M}\right)} - \left(\frac{V_2}{\Omega_S}\right)\left(\frac{\tau_2}{\tau_2\left(1 - \frac{1}{\Omega_M}\right) - \tau_M}\right). \quad (30)$$

To determine the constant of integration k, the value of $V_{M2}$ at the end of $\phi_1$ is $$V_{M2}(0) = V_{M1}(d_{\phi 1}) = V_{\phi 1}, \quad (31)$$

where $d_{\phi 1}$ is the overall time of discharge for $\phi_1$ and $V_{\phi 1}$ is the voltage left on the cell at the end of $\phi_1$. Applying the initial condition to equation 30 and solving for k:

$$k = V_{\phi 1} + \left(\frac{V_2}{\Omega_S}\right)\left(\frac{\tau_2}{\tau_2\left(1 - \frac{1}{\Omega_M}\right) - \tau_M}\right). \quad (32)$$

The solution to the initial-value problem for $\phi_2$ is $$V_{M2}(t) = \left(\frac{V_2}{\Omega_S}\right)\left(\frac{\tau_2}{\tau_2\left(1 - \frac{1}{\Omega_M}\right) - \tau_M}\right)\left(e^{-(t/\tau_M)\left(1 - \frac{1}{\Omega_M}\right)} - e^{-t/\tau_2}\right) + V_{\phi 1} e^{-(t/\tau_M)\left(1 - \frac{1}{\Omega_M}\right)}. \quad (33)$$

Equation 33 provides a means to calculate the residual membrane potential at the end of $\phi_2$ for the cells that were not stimulated by $\phi_1$. Setting Equation 33 equal to zero, we solve for t, thereby determining the duration of $\phi_2$, denoted $d\phi_2$, such that $V_{M2}(d\phi_2) = 0$. By designing $\phi_2$ with a duration $d\phi_2$, the biphasic shock pulse removes the residual change placed on a cell by $\phi_1$. We determine $d\phi_2$ to be:

$$d_{\phi 2} = \left(\frac{\tau_2 \tau_M}{\tau_2\left(1 - \frac{1}{\Omega_M}\right) - \tau_M}\right) \ln\left(1 + \left(\frac{\tau_2\left(1 - \frac{1}{\Omega_M}\right) - \tau_M}{\tau_2}\right)\left(\frac{\Omega_S V_{\phi 1}}{V_2}\right)\right). \quad (34)$$

From the equations above, an optimal monophasic or biphasic defibrillation waveform may be calculated for an external defibrillator. Then the table below illustrates the application of the design rule as the overall chest resistance ranges from 25 Ω to 200 Ω:

| R (Ω) | $\tau_1$ | d($\phi_1$) | $V_{final}$ | $E_{delivered}$ |
|---|---|---|---|---|
| 25 | 5.2 | 5.05 | 757 | 343 |
| 50 | 10.2 | 6.90 | 1017 | 297 |
| 75 | 15.2 | 8.15 | 1170 | 263 |
| 100 | 20.2 | 9.10 | 1275 | 238 |
| 125 | 25.2 | 9.90 | 1350 | 216 |
| 150 | 30.2 | 10.55 | 1410 | 201 |
| 175 | 35.2 | 11.15 | 1457 | 186 |
| 200 | 40.2 | 11.65 | 1497 | 176 |

It should be noted and understood that the design of $\phi_2$ is independent from $\phi_1$. To design $\phi_2$, the only information necessary from $\phi_1$ is where the cell response was left when $\phi_1$ was truncated. Additionally, $\phi_2$ need not use the same or similar circuitry as that used for $\phi_1$. For example, $\phi$ may use circuitry as illustrated in FIG. 4 where $\phi_2$ may use circuitry illustrated in FIG. 5a, or vice-versa. The corresponding design rules for a $\phi_1$ circuitry may be used in conjunction with the design rules for a $\phi_2$ circuitry, regardless of the specific circuitry used to implement each phase of a monophasic or biphasic shock pulse.

PRESENT INVENTION

The present invention is based on the charge burping model hypothesis which postulates and defines an optimal pulse duration for $\phi_2$ as a duration that removes as much of the $\phi_1$ residual charge from the cell as possible. Ideally, the objective is to maintain unstimulated cells with no charge or set them back to relative ground.

A further objective of the present invention is to formulate a measurement by which the optimal duration of a $\tau_S$ (cell time constant) and $\tau_M$ (membrane time constant) can be measured. Although one can choose a proper $\phi_2$ (fixed) for a given cell response $\phi_1$, in transthoracic shock pulse applications, $\tau_M$ is not known and it varies across patients, waveforms and time. For a fixed $\phi_2$, therefore, the error in $\tau_M$ could be substantial. Realizing this, the present invention is designed to correct for "range" of candidate $\tau_M$ values to fit an optimal duration for a fixed $\phi_2$. In other words, $\phi_2$ is selected so that the capacitance in the model is matched with measured $R_H$ to get a "soft landing" to thereby minimize error due to $\tau_M \pm E$ in charge burping ability of $\phi_2$ involving patient variability.

The technique of "soft landing" advanced by the present invention limits the error in $\tau_M$ and sets $\phi_2$ to dynamically adjust within a range of possible $\tau_M$ values. As discussed hereinbelow, optimizing solutions are used to determine parameters on which intelligent calculations could be made so that autonomous $\phi_2$ adjustments for variable $R_H$ are possible.

Figure 3:
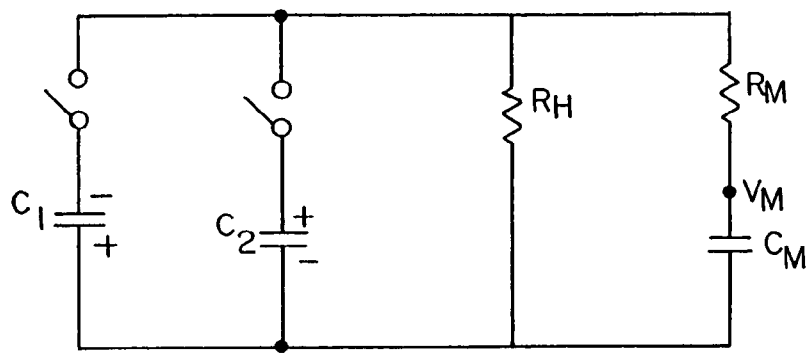
FIG. 3 is a known biphasic defibrillation model.

The charge burping model also accounts for removing the residual charge at the end of $\phi_1$ based on $\phi_2$ delivered by a separate set of capacitors other than those used to deliver $\phi_1$. Referring now to FIG. 3, $C_1$ represents the $\phi_1$ capacitor set and $C_2$ represents the $\phi_2$ capacitor, $R_H$ represents the resistance of the heart, and the pair $C_M$ and $R_M$ represent the membrane series capacitance and resistance of a single cell. The node $V_S$ represents the voltage between the electrodes, while $V_M$ denotes the voltage across the cell membrane.

Accordingly, one of the advantages that AEDs have over ICDs, is that the implementation of a $\phi_2$ waveform may be completely independent of the implementation of $\phi_1$. Specifically, the charging and discharging circuits for $\phi_1$ and $\phi_2$ do not need to be the same circuitry. Unlike ICDs, AEDs are not strictly constrained by space and volume requirements. Within practical limits, in AEDs the capacitance and voltage which characterize $\phi_2$ need not depend on the circuitry and the values of $\phi_1$.

The Lerman-Deale model for AEDs define the main series for current to pass through the chest wall, the lungs and the heart. Further, two shunting pathways in parallel with current pathway through the heart are defined. Another shunting pathway is provided by the thoracic cage. However, when compared to the resistivity of the lungs, the thoracic cage resistance is rather negligible.

Thus, considering the transthoracic defibrillation model of FIG. 4, there are several other resistances in addition to those discussed for the charge burping model hereinabove. $R_S$ represents the resistance of the defibrillation system, including the resistance of the electrodes. $R_{CW}$ and $R_{LS}$ represent the resistances of the chest wall and the lungs, respectively, in series with resistance of the heart, $R_H$. $R_{TC}$ and $R_{LP}$ represent the resistances of the thoracic cage and the lungs, respectively, in parallel with the resistance of the heart.

As discussed hereinabove, developing design equations which enable adjustments for variable resistances encountered in the transthoracic defibrillation model of FIG. 4 is one of the advances of the present invention. In order to adjust for variable $R_H$ both $\phi_1$ and $\phi_2$ are assumed fixed. Then $\phi_2$ is selected to have a range of capacitance values which permit to optimize the slope of the voltage curve at time t. In other words, $C_{S2}$ for $\phi_2$ is chosen such that $$\frac{dv}{dt} = 0$$

The design parameters of the present invention are derived from equation 35, as follows:

$$V_M(t) = V_O(1 - e^{-t/\tau_M}). \quad (35)$$

Equation 35 can be rewritten as:

$$V_{M2}(t) = \quad (36)$$
$$\left(V_{\phi 1} + \left\{\frac{\tau_2}{\tau_2 - \tau_M}\right\}V_2\right)e^{\frac{-\tau}{\tau_M}} - \left\{\frac{\tau_2}{\tau_M - \tau_M}\right\}V_2 e^{-t/\tau_2} = 0.$$

Letting $A = V_{\phi 1} + B$ and $$B = \frac{\tau_2}{\tau_2 - \tau_M} V_2,$$

equation 36 can be written as:

$$V(t) = Ae^{\frac{-t}{\tau_M}} - Be^{\frac{-t}{\tau_2}}. \quad (37)$$

Differentiating equation 37 with respect to t, we have the following:

$$\frac{dv}{dt} = \frac{-Ae^{-t/\tau_M}}{\tau_M} + \frac{B}{\tau_M}e^{-t/\tau_2} = 0. \quad (38)$$

Equation 38 is the profile of $\phi_1$ waveform and at $$\frac{dv}{dt} = 0,$$

the slope of the curve is zero, which means the terminal value of the time constant is determinable at this point. Thus, solving equation 38 for the value of t, we have:

$$t = \left(\frac{\tau_2}{\tau_2 - \tau_M}\right)^{\tau_M} \cdot \ln\left\{\frac{\tau_2}{\tau_M} \frac{\left(V_{\phi 1} + \frac{\tau_2}{\tau_2 - \tau_M} V_2\right)}{\left(\frac{\tau_2}{\tau_2 - \tau_M}\right) V_2}\right\} \quad (39)$$

where $$t_1 = \left(\frac{\tau_2 \tau_M}{\tau_2 - \tau_M}\right) \ln\left\{1 + \left(\frac{\tau_2 \tau_M}{\tau_2}\right)\left(\frac{V_{\phi 1}}{V_2}\right)\right\} \quad (40)$$

$$t_1 = t_1 + \left(\frac{\tau_2 \tau_M}{\tau_2 - \tau_M} \ln\left\{\frac{\tau_2}{\tau_M}\right\}\right). \quad (41)$$

For biphasic defibrillation waveforms, it is generally accepted that the ratio of $\phi_1$, duration ($\tau_M$) to $\phi_2$ duration ($\tau_2$) should be $\geq 1$. Charge burping theory postulates that the beneficial effects of $\phi_2$ are maximal when it completely removes the charge deposited on myocardial cell by $\phi_1$. This theory predicts that $\phi_1/\phi_2$ should be >1 when $\tau_S$ is >3 ms and <1 when $\tau_S$<3 ms. $\tau_S$ is defined as the product of the pathway resistance and capacitance. (See NASPE ABSTRACTS, Section 361 entitled *Charge Burping Predicts Optimal Ratios of Phase Duration for Biphasic Defibrillation*, by Charles D. Swerdlow, M. D., Wei Fan, M. D., James E. Brewer, M. S., Cedar-Sinai Medical Center, Los Angeles, Calif.

In light of the proposed duration ratio of $\phi_1$ and $\phi_2$, wherein the optimal solution is indicated to be at $t_1 = t_2$ where t is the duration of $\phi_1$ and $t_2$ is the duration of $\phi_2$ and superimposing this condition on equation 41 hereinabove, we have:

$$t_2 = t_1 + \left(\frac{\tau_2 \tau_M}{\tau_2 - \tau_M} \cdot \ln\left\{\frac{\tau_2}{\tau_M}\right\}\right)$$

setting $t_2 = t_1$, remanaging terms we have:

$$t_2 - t_1 = 0 = \quad (42)$$

$$\frac{\tau_2 \tau_M}{\tau_2 - \tau_M} \cdot \ln\left\{\frac{\tau_2}{\tau_M}\right\} \text{ or } \tau_2 \tau_M \cdot \ln\left\{\frac{\tau_2}{\tau_M}\right\} \text{ or } \ln\frac{\tau_2}{\tau_M} = 0 \text{ or } \frac{\tau_2}{\tau_M} = 1.$$

From the result of equation 42 we make the final conclusion that the optimal charge burping is obtained when $t_2 = t_M$. From prior definition, we have established that $t_M = R_H C_S$. Thus, in accordance with equation 42, $t_2 = t_M = R_H C_S$.

Figure 6:
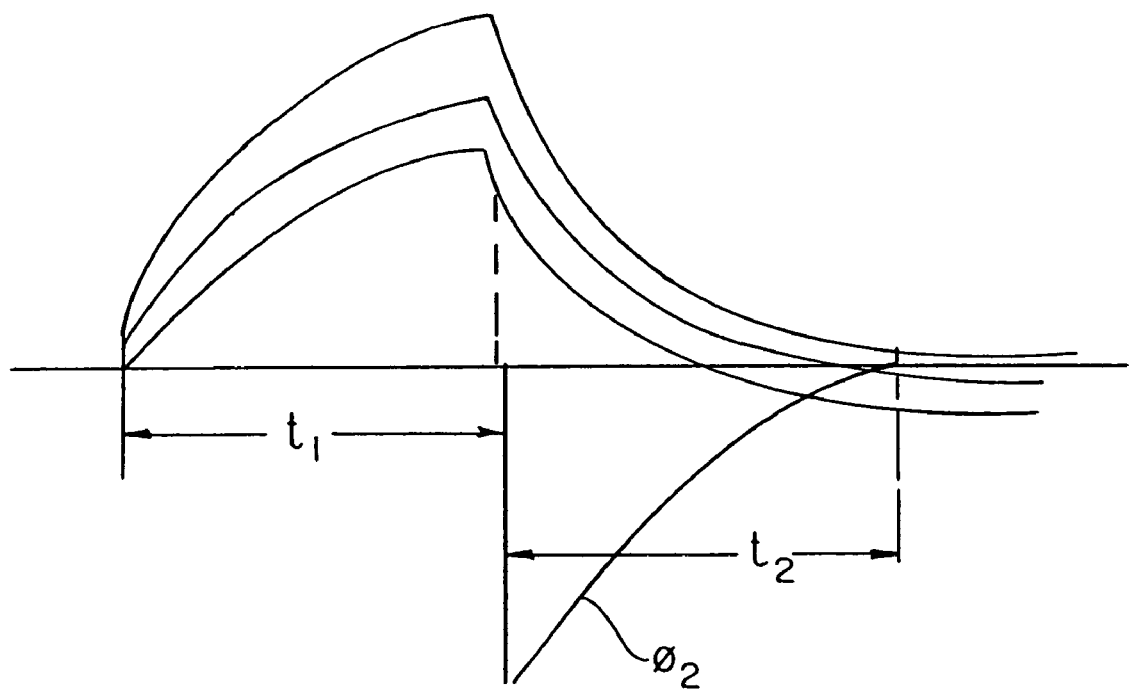
FIG. 6 illustrates a biphasic waveform generated utilizing the present invention.

Referring now to FIG. 6, a biphasic defibrillation waveform generated using the equations 35-42 is shown. At $V_M = 0$ and $dV_M/dt = 0$, $\phi_1$ and $\phi_2$ are equal to zero.

Figure 7:
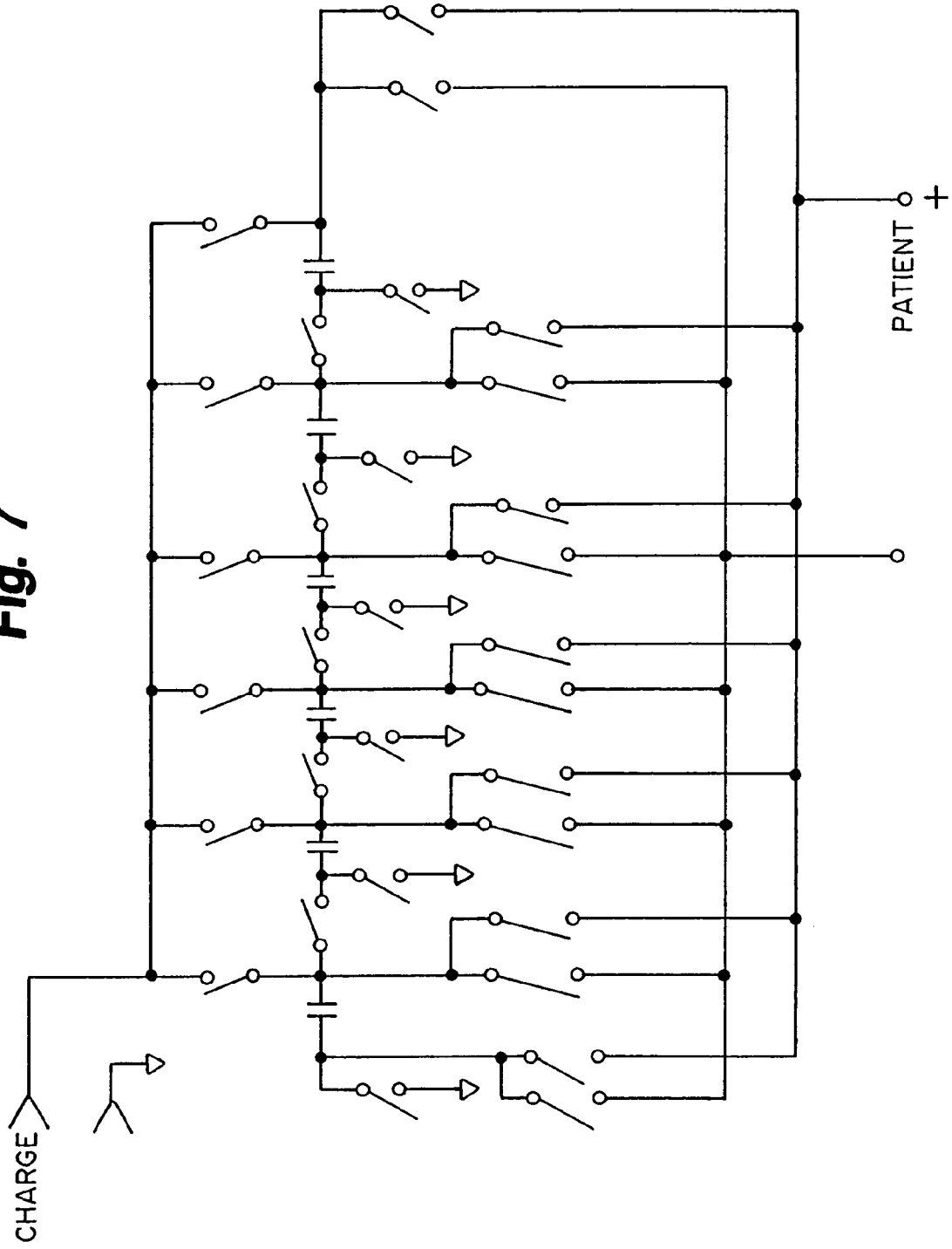
FIG. 7 is a schematic diagram of a circuit which enables the implementation of the present invention.

FIG. 7 is a schematic of a circuit which enables the implementation of the theory developed in the present invention. The circuit shows a plurality of double throw switches connecting a plurality of capacitors. The capacitors and the switches are connected to a charge or potential source. The voltage is discharged via electrodes. One aspect of implementing the "soft landing" charge burping technique developed in the present invention is to fix $C_S$ for $\phi_1$ and fix $C_S$ for $\phi_2$. Further, $t_M$ is fixed. Then a range of resistance values representing $R_H$ are selected. The $t_M$ and $R_H$ ranges represent the patient variability problem. The objective is to enable corrective action such that $C_S$ values could range between 40 uf-200 uf and dv/dt=0 for $t_2$. As indicated hereinabove, the error in charge burping is minimized for $t_2$ when dv/dt=0.

The implementation of the present invention requires that capacitor bank values be determined for $\phi_1$ and $\phi_2$. Specifically, the capacitor values for $\phi_1$ should be designed to realize dv/dt=0 and V=0 for $\phi_2$ to minimize charge burping error due to $R_H$ and $t_M$. Where a variable resistor is used to set $R_H$ thus providing a known but variable value and $t_M$ can be set within these practical ranges.

Figure 8:
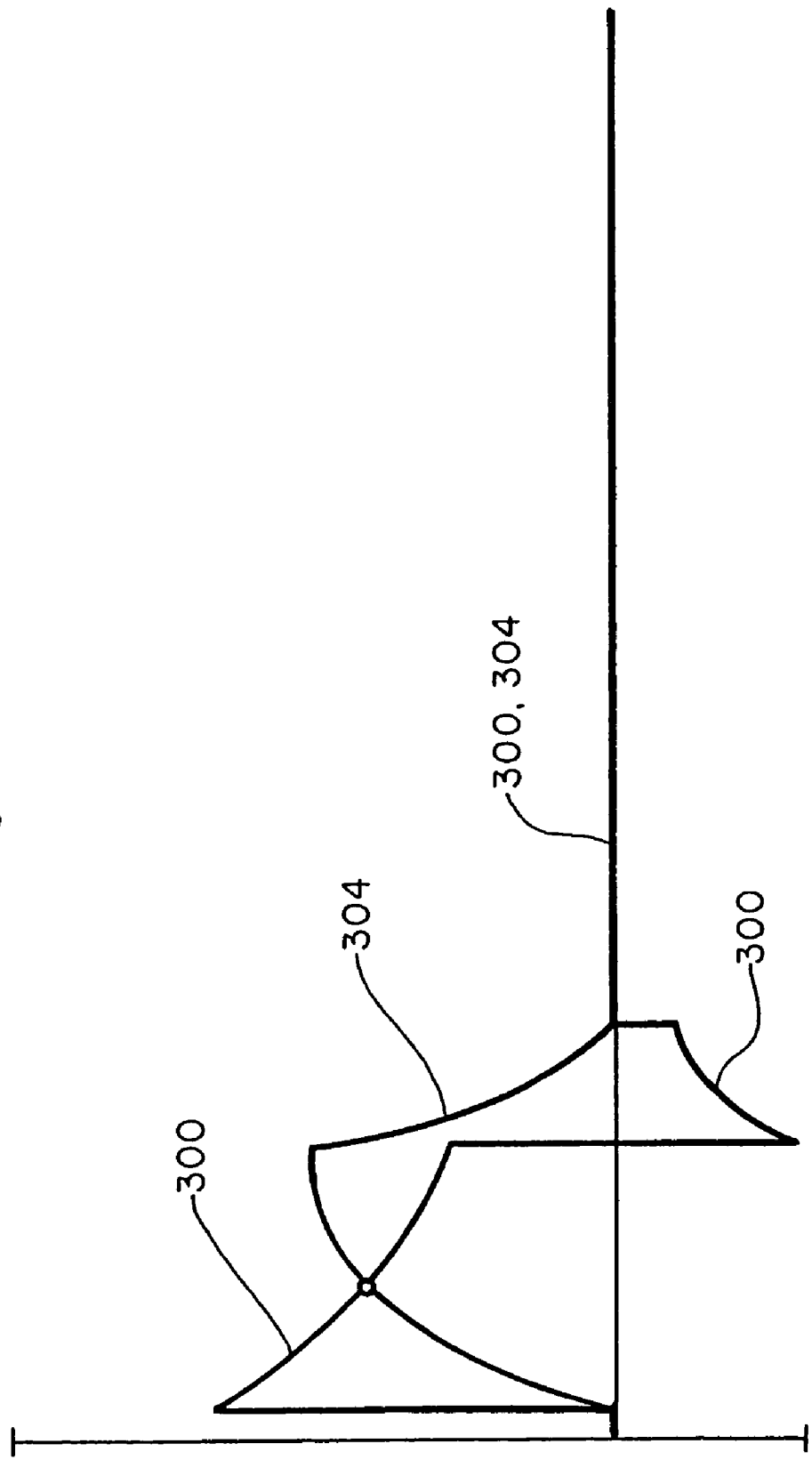
FIG. 8 illustrates a biphasic waveform in relation to a cellular response curve.

FIG. 8 depicts a biphasic defibrillation waveform 300, generated using equations 35-42 above, in relation to a predicted patient's cellular response curve 304; the cellular response, as explained earlier is based on a patient's measured impedance. As shown, the residual charge left on the cardiac cells after delivery of $\phi_1$ has been brought back to zero charge, i.e., charge balanced, after the delivery of $\phi_2$. This charge balance has been achieved because the energy delivered has been allowed to vary.

Traditionally, all defibrillation waveforms have delivered a fixed energy. This has been primarily because therapy has been measured in joules. These fixed energy waveforms, which include monophasic damped sine, biphasic truncated exponential, and monophasic truncated exponential waveforms, only passively responded to patient and/or system impedance.

This passive response was by charging a capacitor to a fixed voltage, wherein the voltage was adjusted depending on amount of fixed energy to be delivered that was desired, and discharging it across the patient, whom acts as the load. The energy delivered is controlled by the simple equation:

$$E = \frac{1}{2} C V^2 \quad (43)$$

where: E is the energy, C is the capacitance of the charging capacitor, and V is the voltage.

In the case of the truncated exponential waveform, equation 43 is extended to:

$$E = \frac{1}{2} C (V_i^2 - V_f^2) \quad (44)$$

where: $V_i$ is the initial voltage and $V_f$ is the final voltage.

Significantly, no form of patient impedance or system impedance appears in either of the above equations.

With respect to system impedance, the above equations make the assumption that the internal impedance of the defibrillator is 0 ohms. This is a good approximation for truncated exponential waveforms, but it is not a good approximation for damped sine waveforms. Damped sine waveforms typically have 10-13 ohms internal impedance. This internal impedance effects the delivered energy. The internal impedance of the defibrillator will absorb a portion of the stored energy in the capacitor, thus reducing the delivered energy. For low patient impedances, the absorbed energy can become quite significant, with on the order of 40% of the stored energy being absorbed by the internal resistances.

With respect to patient impedance, the patient acts as the load and, as such, the peak current is simply a function of the peak voltage via Ohm's law:

$$I = \frac{V}{R} \quad (45)$$

where: I is the current and R represents the patient's impedance.

As equation 45 indicates, the current is inversely proportional to the impedance. This means that there is lower current flow for high impedance patients which, in turn, means that it takes longer to deliver the energy to a high impedance patient. This fact is further exemplified when considering the equation for a truncated exponential voltage at any point in time:

$$V(t) = \frac{1}{2}CV_i e^{-\frac{t}{RC}} \quad (46)$$

Equation 46 shows that patient impedance, R, is reflected within in the voltage equation which forms a part of the energy equation. Equation 46 shows that the duration of a defibrillation waveform extends passively with impedance, since it takes longer to reach the truncate voltage.

To actively respond to system and patient impedances, as the present invention does with its charge burping model, the energy or the voltage must be allowed to vary. However, there is a problem with varying the voltage in that the voltage is set before energy delivery. Thus, making the voltage the more difficult variable to manage. On the other hand, energy may be adjusted on the fly, making it the easier variable to manage. To explain further, in the charge balance waveform of the present invention, there is a desire to exactly terminate the defibrillation waveform when the cellular response curve returns to zero charge, see again FIG. 8 Failing to terminate the defibrillation waveform when the cellular response curve returns to zero charge, e.g., overshooting or undershooting the neutral condition, can promote refibrillation.

In achieving this charge balanced waveform, as explained in detail in the specification above: (1) the charging capacitor is charged to a specific charge voltage, i.e., this specific charge voltage is not a system variable; (2) the current is controlled by the patient impedance $$\left(I = \frac{V}{R}\right),$$

i.e., the current is not a system variable; and (3) the duration of the defibrillation pulse is controlled by the expected cellular response curve, i.e., duration is not a system variable. Because items 1-3 are not system variables but rather are preset or set in accordance to the patient at hand, the energy must be allowed to vary or the defibrillation system is over constrained and charge balancing cannot be achieved over the range of patient impedances. To deliver fixed energy in a charge balanced system would require the ability to vary the charge voltage. Varying the charge voltage is typically not done since this requires knowing the exact impedance in advance of the shock delivery. Many defibrillators measure the impedance during a high voltage charge delivery since this is more accurate than low voltage measurements done prior to shock delivery. Varying charge voltage also requires a more expensive defibrillation circuitry since capacitor costs increase dramatically with voltage.

It should be noted that due to the characteristics of the cellular response curve, the duration of the defibrillation pulse does increase slightly for increases in patient impedance. This increased duration is of a much lesser effect than in a traditional truncated waveform.

As such, to exactly terminate the defibrillation waveform when the cellular response curve returns to zero charge (FIG. 8), the energy of the defibrillation waveform may be allowed to vary in the delivery of the first phase $\phi_1$ or, alternatively, in the delivery of the second phase $\phi_2$.

With respect to the first phase $\phi_1$, the energy is allowed to vary per each patient encounter by setting the time duration $t_1$ of $\phi_1$. As noted by the iterations of equation 42, the optimal ratio of duration of $\phi_1$ and $\phi_2$ occurs when $t_1=t_2$ or when $\tau_2=\tau_M=R_H C_S$ where $R_H$ is the measured variable heart resistance and $C_S$ is the system capacitance including the capacitance of the first bank of capacitors that are operative with the delivery of the first phase. As $\tau_M$ is fixed and $R_H$ is measured, the value of capacitance $C_S$ is matched to the resistance $R_H$. Because the value of the capacitance is matched to the resistance for the delivery of the first phase $\phi_1$, i.e., it is not matched to a desired amount of fixed energy to be delivered, it can be seen that the amount of energy is allowed to vary specific to and per each patient encounter.

Likewise, with respect to the second phase $\phi_2$, the energy is allowed to vary per each patient encounter by setting the time duration of $\phi_2$. As noted by the iterations of equation 42, the optimal ratio of duration of $\phi_1$ and $\phi_2$ occurs when $t_1=t_2$ or when $\tau_2=\tau_M=R_H C_S$ where $R_H$ is the measured variable heart resistance and $C_S$ is the system capacitance including the capacitance of the second bank of capacitors that are operative with the delivery of the second phase $\phi_2$. As $\tau_2$ is fixed and $R_H$ is measured, the value of capacitance $C_S$ is matched to the resistance $R_H$. Because the value of the capacitance is matched to the resistance for the delivery of the second phase $\phi_2$, i.e., it is not matched to a desired amount of fixed energy to be delivered, it can be seen that the amount of energy is allowed to vary specific to and per each patient encounter.

Although the present invention has been described with reference to preferred embodiments, workers skilled in the art will recognize that changes may be made in form and detail without departing from the spirit or scope of the present invention.

What is claimed:

1. A method for dynamically determining a second phase of a transchest external defibrillation biphasic shock pulse which, when applied though electrodes positioned on a patient's torso, will produce a desired response in the patient's cardiac cell membranes, including:
   providing a quantitative model of a defibrillator circuit for producing the external defibrillation shock pulse;
   providing a quantitative model of a patient including a chest component, a heart component and a cardiac cell membrane component;
   providing a quantitative description of a predetermined response of said cardiac cell membrane to said shock pulse; and
   providing instructions comprising:
   computing a quantitative description of a first phase of a transchest external defibrillation shock pulse that will produce said predetermined cardiac cell membrane response, wherein said computation is made as a function of predetermined cardiac cell membrane response, the patient model and defibrillator circuit model; and
   computing a quantitative description of a second phase of a transchest external defibrillation shock pulse based on the first phase.

2. A method for determining a first and a second phase of a biphasic defibrillation shock pulse, one of said first phase and said second phase having variable energy, wherein upon application of said first phase and said second phase of said biphasic defibrillation shock pulse a desired response is produced in a patient's cardiac cell membrane comprising:
providing a quantitative model of a defibrillator circuit for producing said biphasic defibrillation shock pulse;
providing a quantitative model of a patient that includes a variable heart component;
providing a quantitative description of a predetermined response of said cardiac cell membrane to said shock pulse; and
providing instructions for determining a quantitative description of a first phase and a second phase of said biphasic defibrillation shock pulse comprising:
selecting from a group consisting of items (a) and (b) as defined below:
(a) determining a quantitative description of a first phase of said biphasic defibrillation shock pulse that will produce said predetermined response of said cardiac cell membrane, wherein the determination is made as a function of said predetermined response of said cardiac cell membrane, said quantitative model of a defibrillator circuit, and said quantitative model of a patient, and wherein the quantitative description of the first phase provides for setting a time duration for said first phase based on said variable heart component, whereby an amount of energy to be delivered by said first phase varies according to the time duration that is set; and
determining a quantitative description of a second phase of said biphasic defibrillation shock pulse phase on said first phase; and
(b) determining a quantitative description of a first phase of said biphasic defibrillation shock pulse that will produce said predetermined response of said cardiac cell membrane, wherein the determination is made as a function of said predetermined response of said cardiac cell membrane, said quantitative model of a defibrillator circuit, and said quantitative model of a patient; and
determining a quantitative description of a second phase of said biphasic defibrillation shock pulse based on said first phase, wherein said quantitative description provides for setting a time duration for said second phase based on said variable heart component whereby an amount of energy to be delivered by said second phase varies according to said time duration that is set.

3. An automatic external defibrillation system configured for determining a first and a second phase of a biphasic defibrillation shock pulse, one of said first phase and said second phase having variable energy, wherein upon application of said first phase and said second phase of said biphasic defibrillation shock pulse a desired response is produced in a patient's cardiac cell membrane comprising:
means for producing a quantitative model of a defibrillator circuit for producing said biphasic defibrillation shock pulse; means for producing a quantitative model of a patient that includes a variable heart component;
means for producing a quantitative description of a predetermined response of said cardiac cell membrane to said shock pulse; and
instructions for determining a quantitative description of a first phase and a second phase of said biphasic defibrillation shock pulse comprising:
selecting from a group consisting of items (a) and (b) as defined below:
(a) determining a quantitative description of a first phase of said biphasic defibrillation shock pulse that will produce said predetermined response of said cardiac cell membrane, wherein the determination is made as a function of said predetermined response of said cardiac cell membrane, said quantitative model of a defibrillator circuit, and said quantitative model of a patient, and wherein the quantitative description of the first phase provides for setting a time duration for said first phase based on said variable heart component, whereby an amount of energy to be delivered by said first phase varies according to the time duration that is set; and
determining a quantitative description of a second phase of said biphasic defibrillation shock pulse phase on said first phase; and
(b) determining a quantitative description of a first phase of said biphasic defibrillation shock pulse that will produce said predetermined response of said cardiac cell membrane, wherein the determination is made as a function of said predetermined response of said cardiac cell membrane, said quantitative model of a defibrillator circuit, and said quantitative model of a patient; and
determining a quantitative description of a second phase of said biphasic defibrillation shock pulse based on said first phase, wherein said quantitative description provides for setting a time duration for said second phase based on said variable heart component whereby an amount of energy to be delivered by said second phase varies according to said time duration that is set.

4. A defibrillation apparatus for delivering a biphasic defibrillation shock pulse to produce a desired response in a patient's cardiac cell membrane, wherein a second phase of said biphasic defibrillation shock pulse has a variable energy, comprising:
a defibrillator circuit; and
a pair of electrodes operably coupled to said defibrillator circuit, wherein said pair of electrodes delivers said biphasic defibrillation shock pulse to said patient's cardiac cell membrane;
instructions comprising:
configuring said defibrillator circuit according to:
a quantitative model of a defibrillator circuit for producing said biphasic defibrillation shock pulse;
a quantitative model of a patient that includes a variable heart component; and
a quantitative description of a predetermined response of said cardiac cell membrane to said shock pulse;
a quantitative description of a first phase of said biphasic defibrillation shock pulse that will produce said predetermined response of said cardiac cell membrane, wherein said quantitative description of said first phase has been determined from said predetermined response of said cardiac cell membrane, said quantitative model of said defibrillator circuit, and said quantitative model of said patient; and
a quantitative description of a second phase of said biphasic defibrillation shock pulse wherein said quantitative description of said second phase has been determined based on said first phase and wherein said quantitative description of said second phase includes a time duration setting that has been based on said variable heart component whereby an amount of energy to be delivered by said second phase varies according to said time duration setting.

* * * * *